United States Patent [19]
Toomim et al.

[11] Patent Number: 5,505,208
[45] Date of Patent: Apr. 9, 1996

[54] METHOD FOR DETERMINING MUSCLE DYSFUNCTION

[75] Inventors: Hershel Toomim, Los Angeles; John D. Kasten, Laguna Niguel; Gerald D. Appel, Beverly Hills; Daniel Levendowski, Los Angeles, all of Calif.

[73] Assignee: Toomin Research Group, Culver City, Calif.

[21] Appl. No.: 166,347

[22] Filed: Dec. 10, 1993

[51] Int. Cl.⁶ ........................................................ A61B 5/04
[52] U.S. Cl. ............................................. 128/733; 128/774
[58] Field of Search ................................... 128/733, 734, 128/774, 781, 782

[56] References Cited

U.S. PATENT DOCUMENTS

| | | | |
|---|---|---|---|
| 4,148,303 | 4/1979 | Cohen | 128/733 |
| 4,664,130 | 5/1987 | Gracovetsky | 128/733 |
| 4,667,513 | 5/1987 | Konno | 128/774 |
| 5,085,225 | 2/1992 | DeLuca et al. | 128/733 |
| 5,086,779 | 2/1992 | DeLuca et al. | 128/733 |
| 5,163,440 | 11/1992 | DeLuca et al. | 128/733 |
| 5,335,667 | 8/1994 | Chu et al. | 128/734 |

*Primary Examiner*—Max Hindenburg
*Attorney, Agent, or Firm*—Pillsbury Madison & Sutro

[57] ABSTRACT

A method for collecting back muscle dysfunction which comprises collecting electrical muscle activity measurements by applying a plurality of electrodes in a pattern across a patient's back or test subject's back, and measuring the electrical activity at each of these electrodes and storing these measurements at the same time. The database of these sets of measurements from the number of individuals is generated so that a normative sample for comparison is formed. A patient's back muscle activity is quantified by collecting electrical muscle activity measurements for the patient and comparing the patient's electrical muscle activity measurements ratios to the sample average ratios of the normative group.

23 Claims, 12 Drawing Sheets

121 Cervical Paraspinal
122 Upper Trapezius
123 Middle Trapezius
124 Teres Major
125 Thoracic Paraspinal
126 Latissimus Dorsi
127 Obliquus Externus
128 Sacral Paraspinal

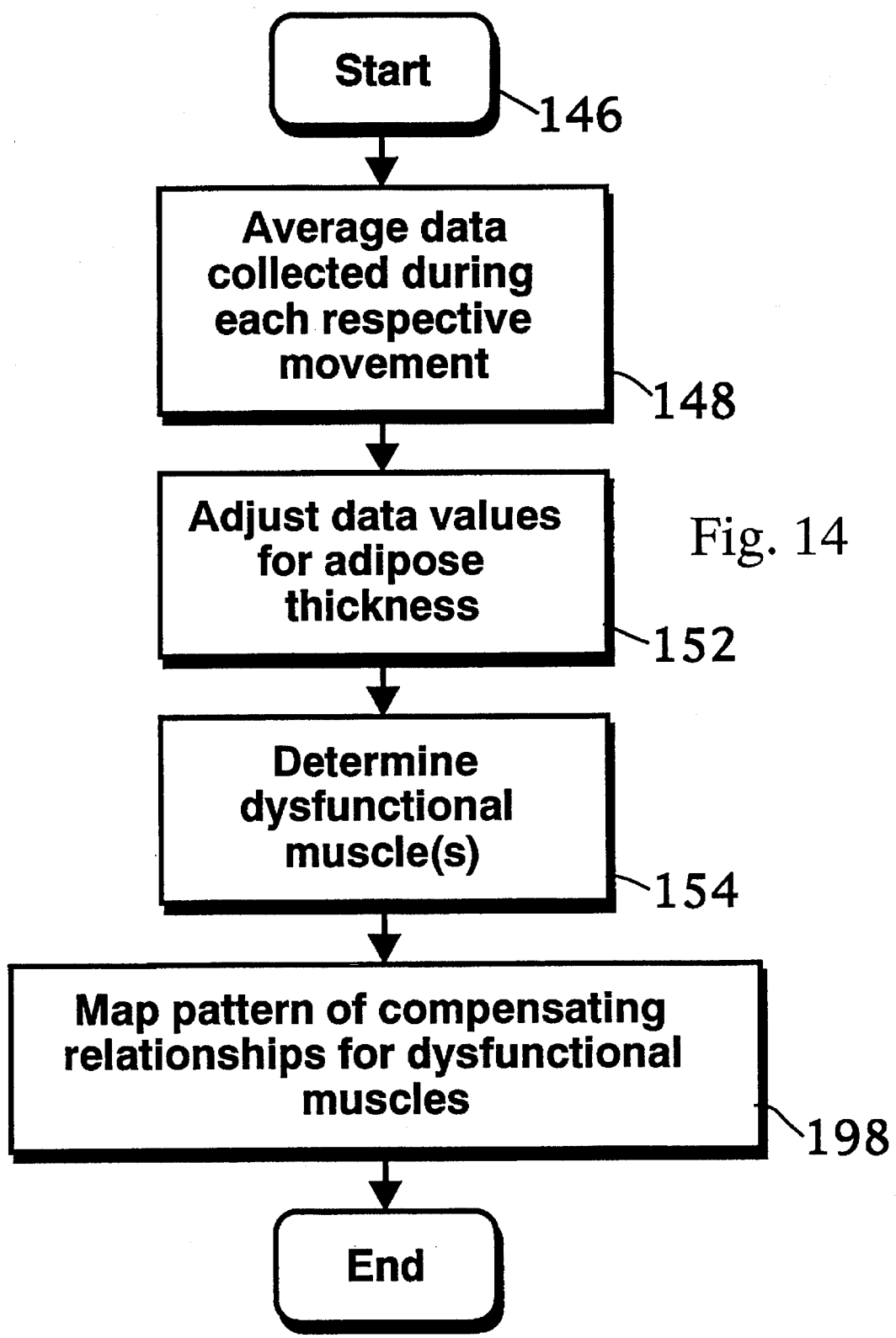

METHOD FOR DETERMINING MUSCLE DYSFUNCTION

BACKGROUND OF THE INVENTION

The present invention relates generally to the field of medical equipment for evaluating muscle performance. More particularly, the present invention relates to a method for determining back muscle dysfunction.

Electrical activity measurements as a measure of muscle activity, electromyographic (EMG) measurement, may be performed using invasive or non-invasive techniques. EMG measurements are used in number of different medical applications.

The use of invasive percutaneous EMG has widespread medical acceptance as an accurate technique for measuring electrical activity of an underlying muscle. However, invasive techniques are often not easily usable. That is, invasive techniques require additional materials, expertise, and risk not found with non-invasive techniques.

Measuring muscle activity using surface EMG (sEMG) measurements has attracted interest in scientists and medical practitioners for the last 30 years with its promise as an objective non-invasive muscle measurement technique. Considerable effort has been expended researching the application of EMG measurements (both percutaneous and non-invasive) in the treatment and possible diagnosis of low back pain. An extensive body of scientific literature now exists describing the use of EMG measurements.

Measurements of surface electrical activity, or any other clinical measurement, must meet several objectives and criteria relating to reliability in order to obtain useful diagnostic or evaluative information. For example, the electrical activity signal measured must be objectively defined and reproducible. The information obtained must meet a need which is best obtainable by using the surface EMG technique. Further, the information must be usable and easily interpreted by the level of skill of practitioners for which it is intended. And, finally, the process must be cost effective and have universal application as either an assessment or therapeutic system or both.

In order to meet these objectives the evaluation system must reliably differentiate between healthy normal pain free subjects and subjects with muscle disorders and report results with an extremely high level of statistical certainty. Of the many possible uses to which surface EMG may be applied, back function evaluation is highly suitable. A relatively large percentage of individuals experience back pain which could be attributed to soft tissue damage, i.e., muscle dysfunction. Typical evaluation techniques are not able to objectively determine the muscle dysfunction responsible for the pain.

Typical clinical evaluation techniques have relied upon subjective evaluations by the patient to determine the nature of the dysfunction. That is, the patient is asked to perform certain motions, and depending upon the patient's ability to perform these motions within subjective pain parameters a diagnosis is generated.

Further, from an economic standpoint a large percentage of insurance claims are made by individuals claiming to have muscle back pain. Because of the subjective nature of the testing, these claims cannot be objectively verified. Accordingly, there is a large potential for fraudulent claims being filed at a substantial cost to insurance companies.

In order to provide an effective assessment system there must be a capability of making significant comparisons of the individual to a normative group. In order to make these comparisons the coefficient of variation, the standard deviation/mean, must lie in the 10%–30% range. Accordingly, it is extremely important that a system have reproducible data.

In the past, studies which have attempted to achieve the reproducibility or minimize the variation in data use a maximum voluntary contraction (MVC) method of normalization. This technique requires high levels of activation and causes the engagement of fast twitch motor units not ordinarily activated in normal movements. That is, these studies compare the measured muscle activity during evaluation to a maximum voluntary contraction.

In normal muscle the slow twitch motor units produce most of their fused tension before fast twitch motor units start to add to muscle force. Addition of fast twitch motor units in MVC causes a disproportionate increase in the surface EMG. The inclusion of fast twitch motor units, which are seldom used in everyday functioning, occurs with the MVC condition and influences the anatomical distribution and force-voltage relationship of EMG data. Moreover, MVC runs the risk of exacerbating pain and doing further damage to dysfunctional muscles.

Clinical use of surface EMG has failed to produce a sufficiently objective evaluation of muscle health. In much of the covering literature relating to back muscle evaluation, an equivalence is sought between EMG resting levels and painful muscles or back pain in general. However, static resting measurements are greatly influenced by small postural adjustment that cannot be adequately controlled. Accordingly, the postural and instrumental error can become so large so as to obscure useful information.

Accordingly, there is a need to develop a system for correctly detecting muscle dysfunction with a high degree of reproducibility. Further, this method also must allow for normalization of data using normally activated muscle values.

SUMMARY OF THE INVENTION

The principal object of the present invention is to provide a method for determining back muscle dysfunction.

Additional objects and advantages of the invention will be set forth in part in the description which follows, and in part will be obvious from the description, or may be learned by the practice of the invention. The objects and advantages of the invention may be realized and obtained by means of the instrumentalities, procedures, and combinations particularly pointed out in the appended claims.

To achieve the objects in accordance with the purpose of the invention, as embodied and described herein, the method for determining back muscle dysfunction comprises the steps of collecting electrical muscle activity measurements for an individual, the measurements being organized into sets of electrical measurements; compiling a database of sets of measurements from a plurality of individuals for making diagnostic comparisons of data; and quantifying back muscle dysfunction for a patient. The step of collecting electrical and muscle activity measurements for an individual includes the substeps of applying a predetermined number of electrodes in a pattern across the individual's back, measuring the electrical activity at each of the plurality of electrodes, and storing measurement of electrical activity from the pattern electrodes as a set of measurements. A set of measurements including the predetermined number of values respectively, corresponding to measurements of electrical activity is made at substantially the same time from each of the plurality of electrodes in the pattern. The step of compiling a database of sets of measurements from a plurality of individuals for making diagnostic comparison of data includes the substeps of repeating the step of collecting electrical muscle activity measurements for sufficient number of individuals to develop a sample representation of a population, computing ratios of electrical muscle activity measurements for each individual's corresponding set of measurements, calculating sample average ratios by averaging corresponding computed ratios of muscle activity measurements, and storing the sample average ratios. The step of quantifying back muscle dysfunction for a patient includes the substeps of repeating the step of collecting electrical muscle activity measurements of a patient, computing ratios of electrical muscle activity measurements for the patient's corresponding set of measurements, comparing the patient's electrical muscle activity ratios to the sample average ratios of the sample, and determining a measure of back muscle dysfunction in response to the comparison of the patient's ratios.

In a further aspect of the invention the method for determining back muscle dysfunction of a patient comprises the steps of measuring electrical muscle activity for an individual, the electrical muscle activity simultaneously determining the functionality and consequent compensating relationships of the muscles in the upper, middle and lower back; calculating ratio data by determining the ratio of selected measures of the electrical muscle activity to selected other measures of the electrical muscle activity for the individual; compiling a sample database of ratio data from a plurality of individuals for making evaluative comparisons of ratio data; repeating the steps of measuring electrical muscle activity and calculating ratio data for the patient; and determining a level of back muscle dysfunction of the patient.

The accompanying drawings, which are incorporated in and constitute a part of the specification, illustrate one embodiment of the invention and, together with the description, serve to explain the principles of the invention.

BRIEF DESCRIPTION OF THE DRAWINGS

FIG. 14 is a flow chart illustrating a procedure for analyzing data in a preferred embodiment of the present invention;

BRIEF DESCRIPTION OF EXEMPLARY PREFERRED EMBODIMENTS

Reference will now be made to a present preferred embodiment of the invention, an example of which is illustrated in association with the accompanying drawings.

Figure 1:
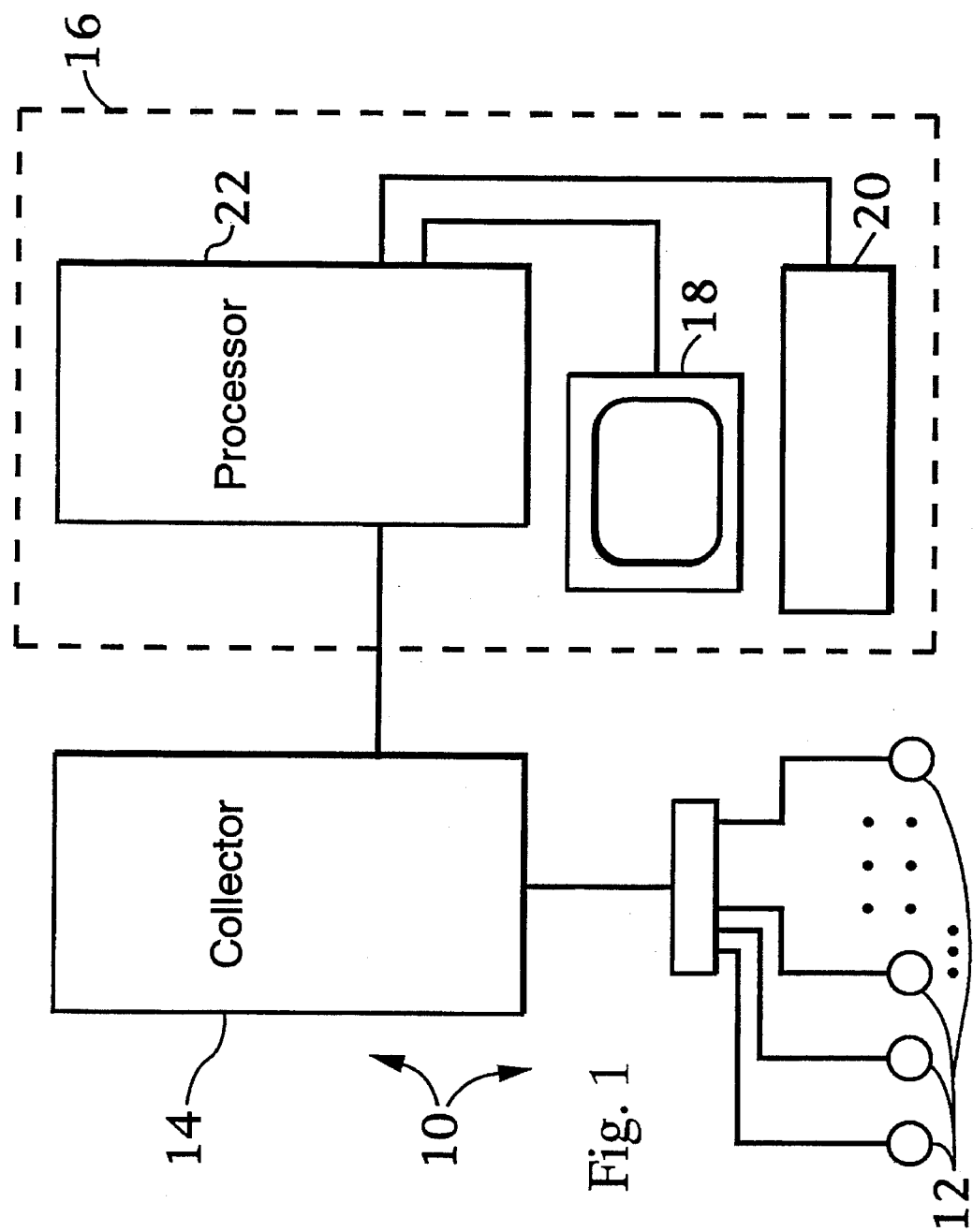
FIG. 1 is an illustration of the apparatus used to practice the method of the present invention.

A preferred embodiment of the method for determining back muscle dysfunction is practiced using the apparatus illustrated by way of example in FIG. 1 and is represented generally by numeral 10.

Back muscle dysfunction analysis system 10 includes electrodes 12, collector 14, and processing system 16. Processing system 16 includes a video display screen 18, keyboard 20, and processor 22. Video display screen 18 is a conventional display such as, for example, a cathode ray tube (CRT) or liquid crystal display (LCD).

In accordance with the invention, a step in determining back muscle dysfunction is measuring electrical muscle activity for an individual and collecting the measurements. These measurements can be organized into sets of electrical measurements. A sub step in collecting the electrical muscle activity measurements, is applying electrodes 12 in a pattern across an individual's back.

Figure 2:
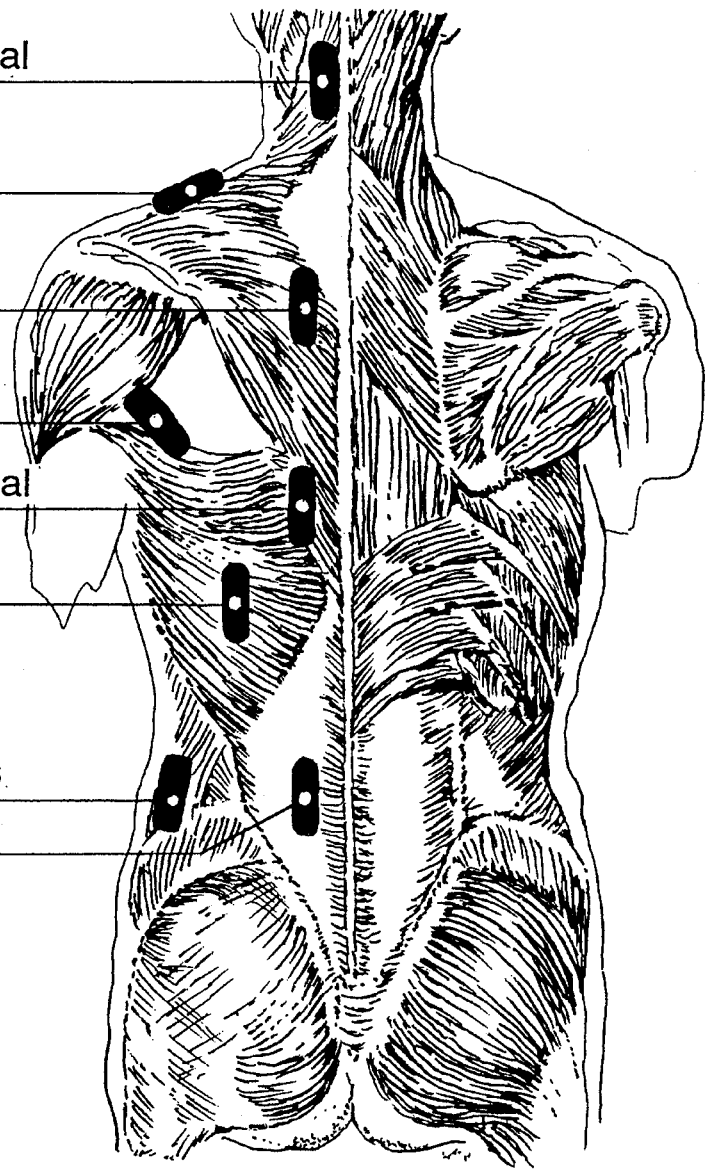
FIG. 2 illustrates the pattern of electrode placements according to the present preferred embodiment of the invention.

FIG. 2 is an anatomical diagram of the muscles of the back illustrating the pattern of electrode placements according to a present preferred embodiment of the invention. Electrodes 12 are illustrated by blackened ovals. The white center portion of these ovals is where the electrode is centered.

Electrodes 12 are named in accordance with the corresponding muscles which they are located over. The left side of the pattern of electrodes is illustrated in FIG. 2 and includes: cervical paraspinal electrode 121, upper trapezius electrode 122, middle trapezius electrode 123, teres major electrode 124, thoracic paraspinal electrode 125, latissimus dorsi electrode 126, obliquus externus electrode 127, lumbar paraspinal electrode 128.

A matching number of electrodes is present on the right side in equivalent positions. Thus, sixteen electrodes are placed on the back of the individual or patient whose surface EMG signals are being measured.

Electrodes 12 are electromyographic surface electrodes which make contact with the surface of the individual's skin. Each of the electrodes 12 include a positive and negative contact across which the potential is measured (step 136). Electrodes 12 detect electrical activity changes, i.e., voltage changes between the two (2) contacts of each electrode. Typically, the detected magnitude of electrical activity is in the range of 0–500 microvolts.

Measurement of electrical potential changes, i.e., electrical activity, generated by muscles is termed electromyographic (EMG) measurement. The measurement of electrical activity on the surface of the skin generated by underlying muscles at each of the plurality of electrodes 12 is surface electromyography (sEMG).

Alternative electrode configurations are contemplated which may correspond to equivalents known in the art. For example, single contact type electrodes may be used which measure electrical potentials with reference to a single common reference.

In a clinical setting, precise placement of percutaneous electrodes to measure electrical muscle activity is difficult and error prone. Studies have shown that surface EMG activity correlates well with muscle activity for underlying muscle groups and does not require a high degree of accuracy in placement, especially when used in a pattern.

The electrodes of the present invention may be applied individually as may be the case with illustrated electrodes 12 or may, in an alternate embodiment, be mounted in an electrode jacket, not shown. The electrode jacket is worn by the individual and has electrodes similar to electrodes 12 mounted therein in the desired pattern. The electrodes of the electrode jacket make contact in the appropriate locations when the individual wears the jacket.

Figure 13:
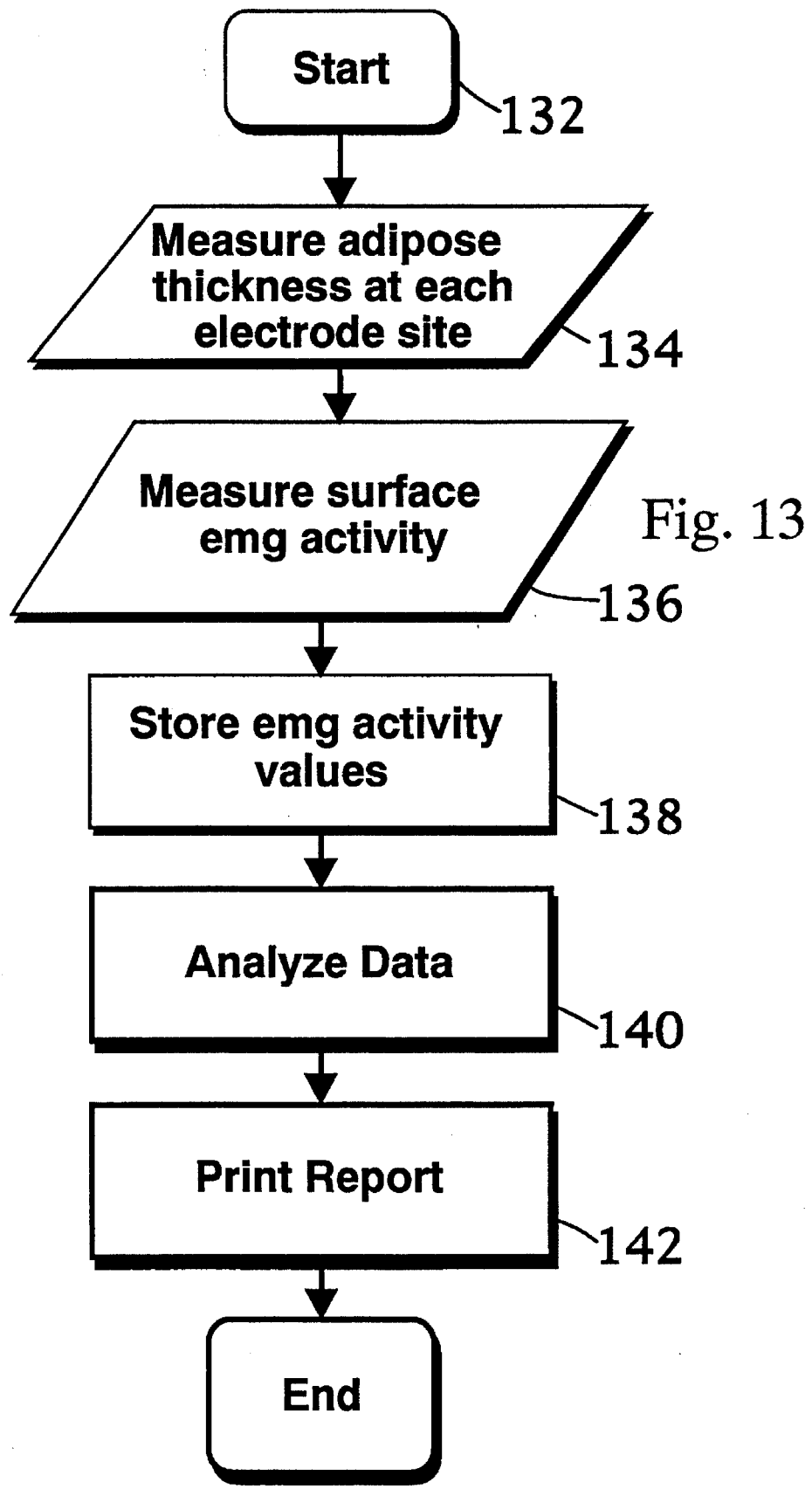
FIG. 13 is a flow chart illustrating a basic procedure for implementing a preferred embodiment of the present invention.
Figure 15A:
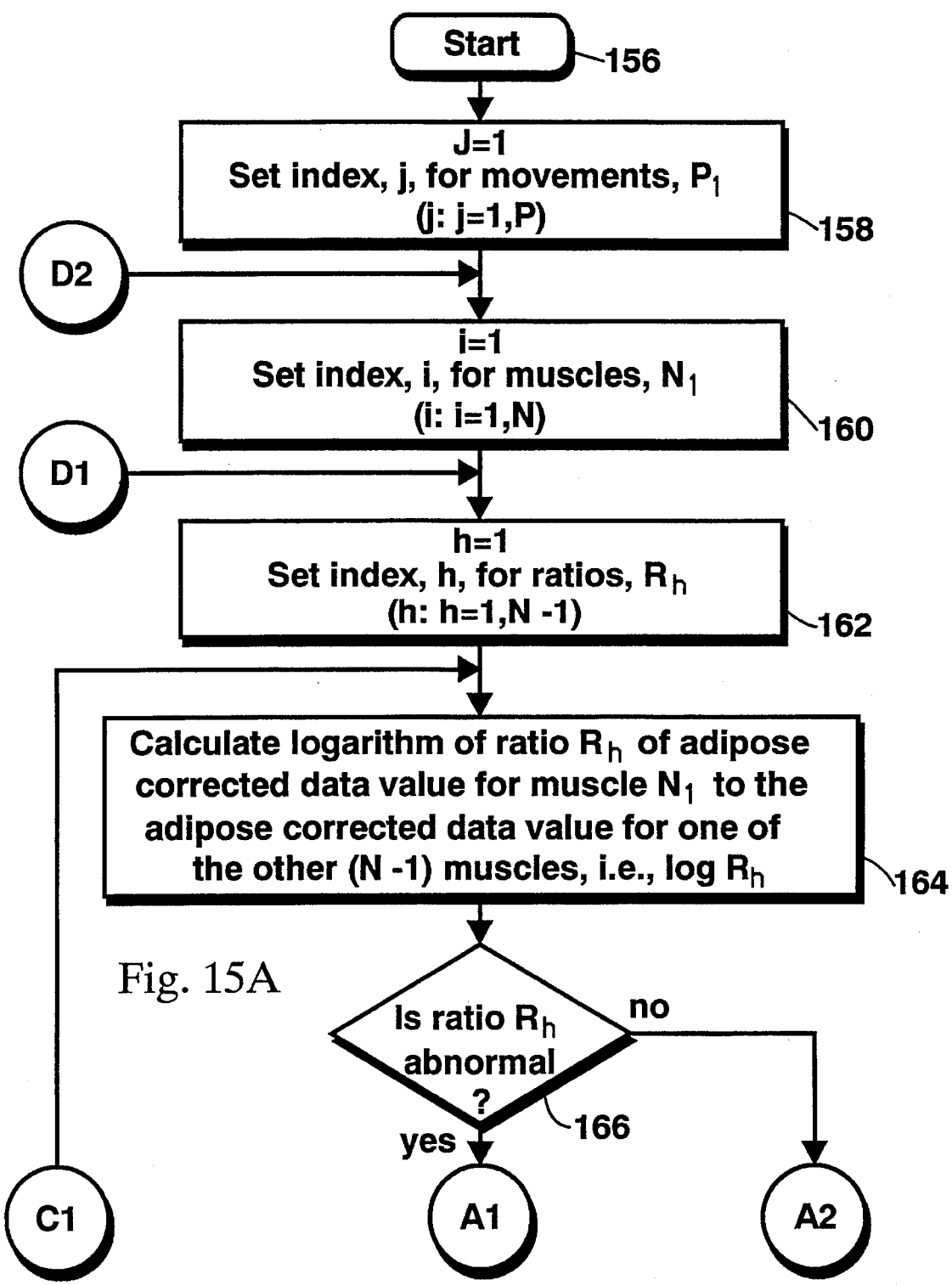
FIGS. 15A–15D are a flow chart illustrating a procedure for determination of dysfunctional muscles in a preferred embodiment of the present invention.
Figure 15B:
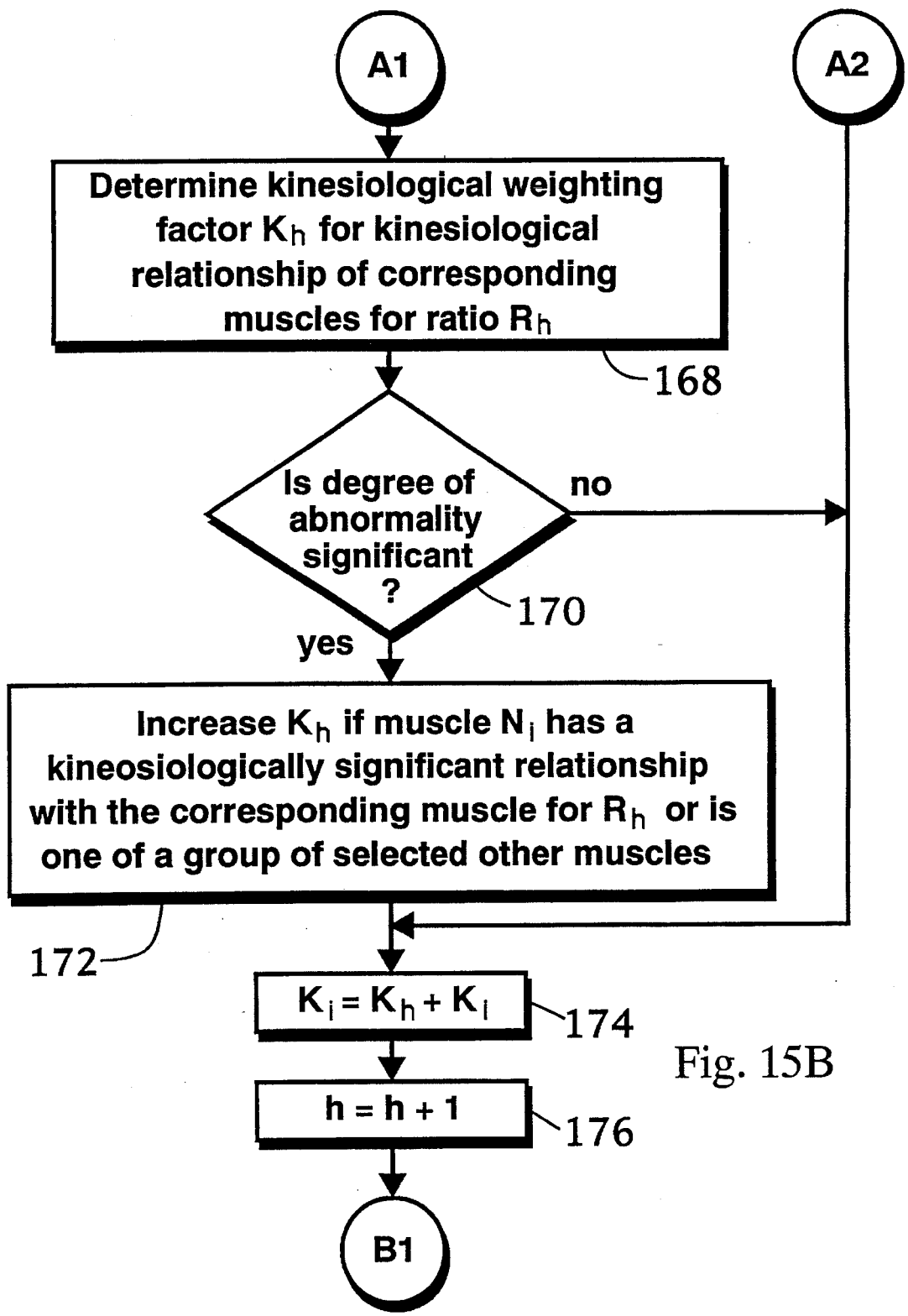
Figure 15C:
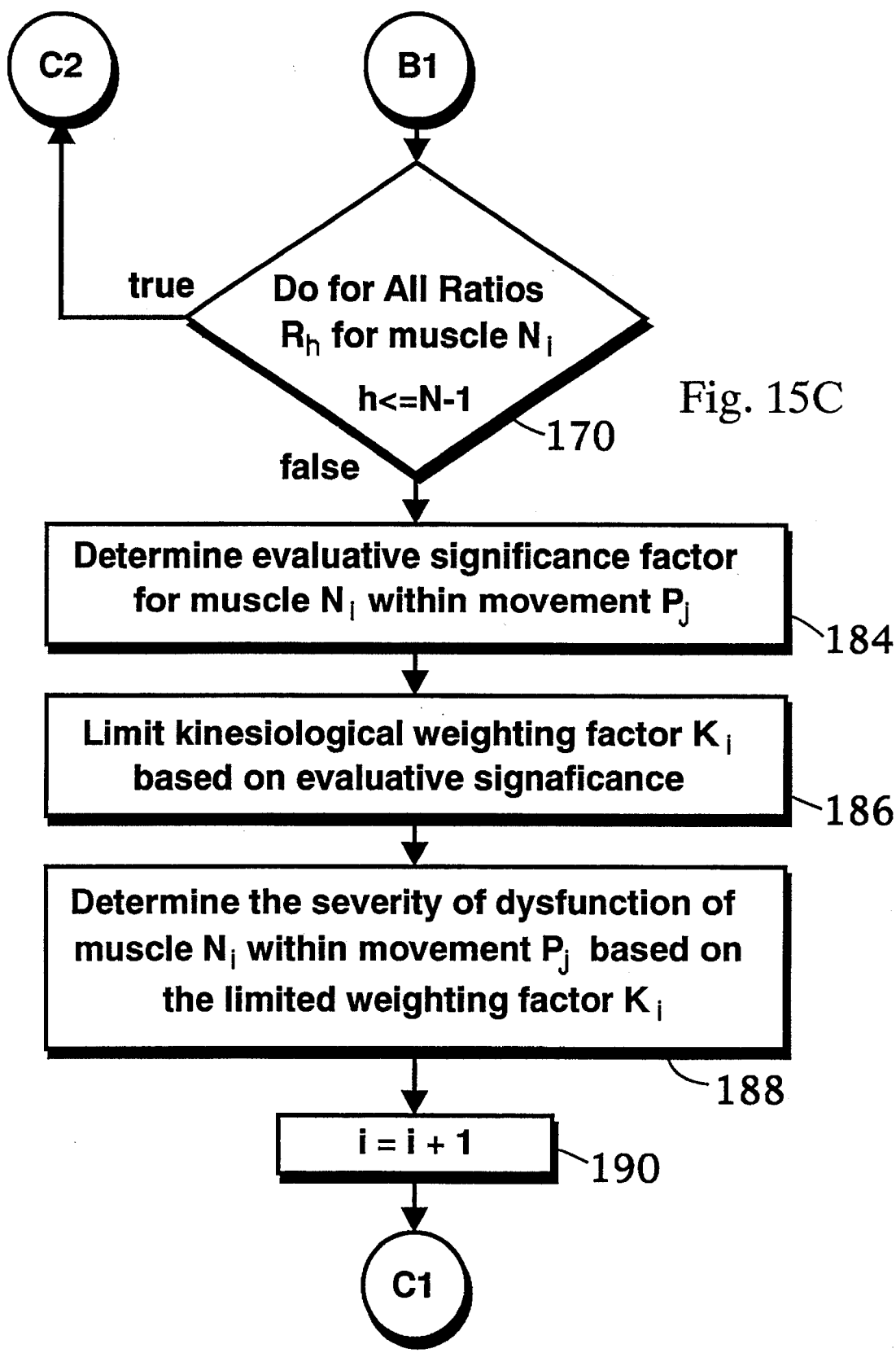
Figure 15D:
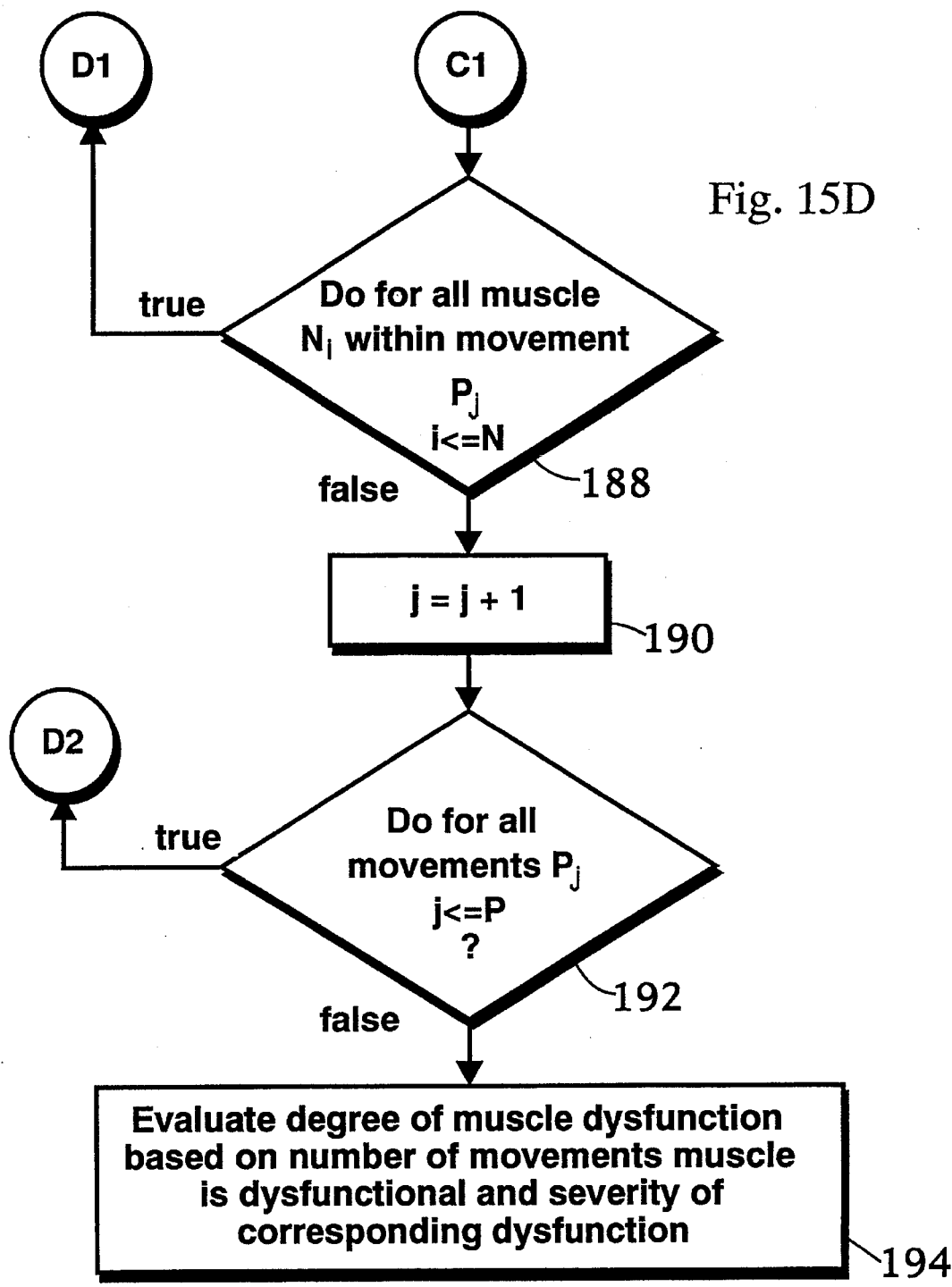

FIG. 13 illustrates a basic procedure for implementing a preferred embodiment of the present invention. After beginning the procedure for determining back muscle dysfunction (step 132) the adipose thickness at each of the sites for electrodes 12 should be measured (step 134).

Adipose tissue can affect the transmission of electrical activity from the underlying muscle. The adipose tissue increases the resistance between the underlying muscle and the corresponding electrode on the surface of the skin. A correction factor can be computed for a given adipose tissue thickness which can be applied to every measurement from the corresponding electrode. This correction factor can be derived from an empirically generated formula and stored in the computer in a table of correction factors corresponding to various thicknesses of adipose tissue.

The measurement of electrical activity over a muscle can be indicative of the health of that muscle. More particularly, depending upon how the measurement is taken and when the measurement is taken, a wide variety of information may be obtained regarding the health of a muscle. Muscle dysfunction can be detected if the muscle has a relatively low electrical output(hypoactivity), high electrical output(hyperactivity), rough signal, or change in the relaxation time after activity.

If the electrical activity measured at the muscle has an unusual amount of fine amplitude variations, the signal is said to be a rough signal. The amount of roughness in the detected electrical signal is also an indication of muscle dysfunction.

If a muscle is damaged, the surface electrode activity may indicate muscle substitution. Muscle substitution occurs when another set of muscles is used to compensate for the lack of functionality due to the damage to a muscle. Accordingly, muscle substitution can be a measurable indication of damage as well as an indication of the nature and location of the damage.

Figure 3:
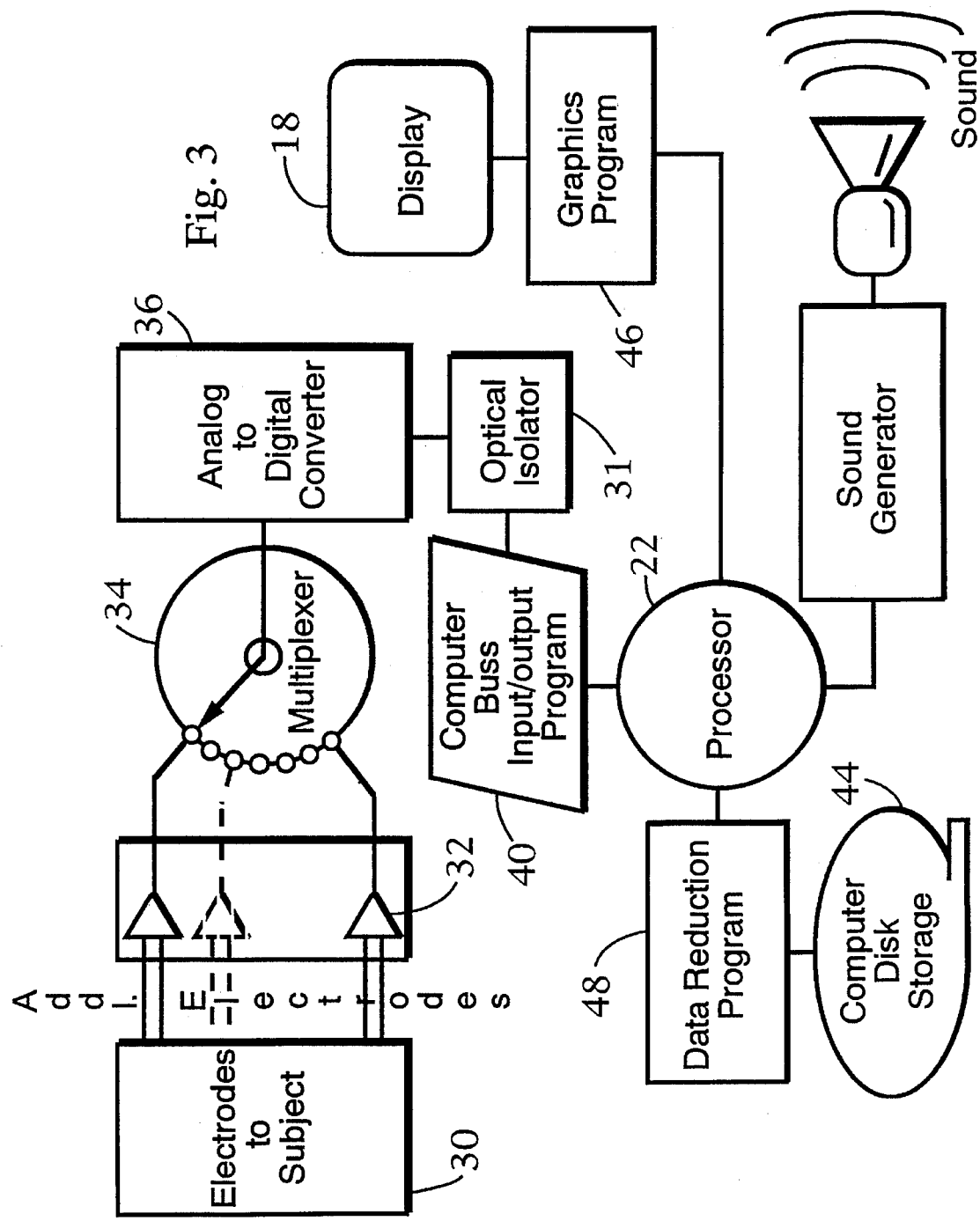
FIG. 3 is a block diagram illustrating some of the components of an apparatus for practicing the present preferred embodiment of the invention.

FIG. 3 is a block diagram illustrating some of the components of collector 14 and processor 22. The voltage detected by electrodes 12 is transmitted with collector 14. In collector 14 the transmitted analog voltage signals from electrodes 12 are amplified. Preferably, amplifier module 30 receives signals from electrodes 12 and amplifies them into the 0 to 4 volt range. Amplifier module 30 includes individual amplifier circuits 32 each of which amplify the signal from electrodes 12.

An additional electrode is required in order to cancel common mode variations for the signals detected by electrodes 12. That is a common mode drive electrode (not shown) is attached to the patient's back.

The amplified analog output signals from amplifier module 30 are fed to a multiplexer 34 which selects one of the signals from amplifier module 30.

Amplified signals from amplifier module 30 are transmitted through multiplexer unit 35 to analog to digital converter 36. Analog to digital converter 36 converts the received analog signal into a digital signal which is transmitted to optical isolator 38.

Electrodes 12 are optically isolated from analysis system 16 by optical isolators 38. In a preferred embodiment of the invention, optical isolator 38 is located after analog to digital convertor 36. Optical isolator 38, which is used in a present preferred embodiment, is a Biocomp Telemeter 2001 Optical Isolator.

Optical isolator 38 electrically separates electrodes 12 from processor system 22. That is, there is no direct electrical connection between the electrodes and the output signal from optical isolator 38. Within optical isolator 38 the input signal activates light emitting diodes (LEDs), not shown, which transmit a light signal to a photodetector, not shown, which converts the light signal into an electrical signal.

In an alternate embodiment, optical isolator 38 receives analog signals and linearly converts them using feedback techniques into analog light signals which are received by a photodetector. The photodetector then outputs an analog electrical signal. This output analog signal can then be fed into an analog to digital converter.

In a preferred embodiment of the present invention the output of optical isolator 38 is transmitted to computer bus interface 40 which transmits digital signals between collector 14 and processor 22. Processor 22 uses a software multiplexer 42 to select the received signals from computer bus interface 40. Preferably, software multiplexer 42 is a program executed by processor 22 to select given inputs at predetermined times so that the signal is forming a time division multiplexed.

Data is transmitted from electrodes 12 to software multiplexer 42 in sequences of four (4) signals. Thus, hardware multiplexer 34 selects a corresponding output of amplifier circuits 32 and transmits groups of signals in sequence through analog to digital converter 36, optical isolator 38 and computer bus interface 40. Software multiplexer 42 then selects these signals in sequence. In order for the full set of data from all electrodes in the pattern to be read, sequences of signals must be transmitted to software multiplexer 42, each sequence corresponding to the outputs from module 30.

In accordance with a preferred method of the present invention, the step of storing measurements of electrical activity from the pattern electrodes as a set of measurements is executed. The set of measurements includes the predetermined number of values respectively, corresponding to measurements of electrical activity made at substantially the same time from each of the plurality of electrodes in the pattern.

In a preferred embodiment, the digital signals received by processor 22 are displayed on display 18 and stored on patient disc 44 (step 138). Graphic program 46 uses the data received through software multiplexer 42 to generate a graphical display of the variation in electrical signals. Data reduction program 48 compresses data to be stored on patient disc 44.

Processor 22 stores the raw data and calculations on this data. Both the raw data and the results of the calculations are stored on patient disc 44.

As discussed previously, the raw data is received through software multiplexer 42. The data received is stored in processor 22 in conventional memory. The rate at which the data is stored and sampled is such that no substantial change will have occurred in the muscle between sample times. Sampling rates will not have to be considered if the data is received and processed in parallel.

Accordingly, the electrical activity measurements from the pattern of electrodes are grouped so each group has measurements which have been taken at substantially the same time. In a preferred embodiment of the invention, the individual performs a predetermined set of movements during collection of electrical muscle activity measurements. Preferably, these movements are carried out with interspersed rest periods and static periods. For example, the movement is carried out for eight seconds and then the individual rests for eight seconds.

Electrical activity measurements are made during static periods within the movements. This dynamic measurement gives a more accurate picture of the muscle action. Relaxed measurements are subject to small postural variations which are hard to correct.

Figure 5:
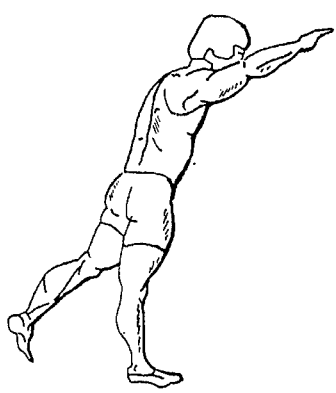
FIG. 5–12 illustrates motions performed in accordance with a preferred embodiment of the present invention.
Figure 6:
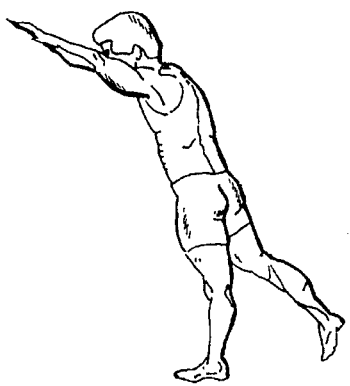
Figure 7:
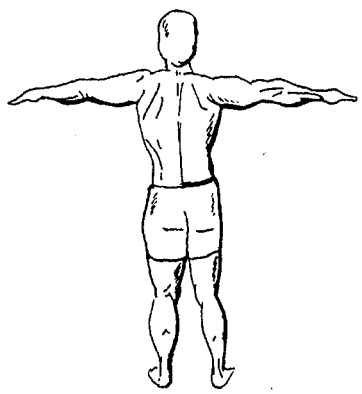
Figure 8:
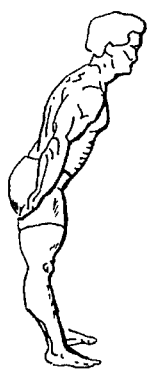
Figure 9:
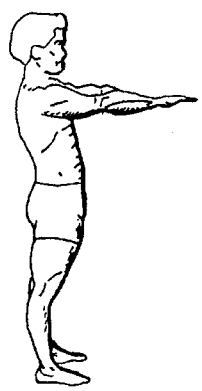
Figure 10:
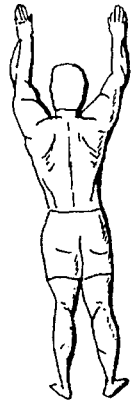
Figure 11:
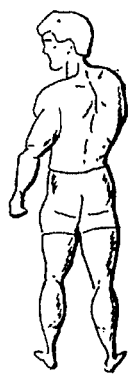
Figure 12:
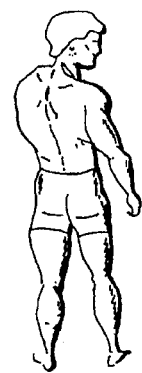

FIGS. 5-12 illustrate the movements used during the dynamic measurements. FIG. 5 illustrates the left "Peter Pan" in which the individual's right arm is overhead, and his left arm and left leg are back. FIG. 6 illustrates the right "Peter Pan" in which the individual's left arm is overhead. FIG. 7 illustrates an arm abduction in which both arms are raised from the sides to a 90-degree angle from the body with the palms of the hand facing down. FIG. 8 illustrates the bow in which the individual bows 45-degrees forward at the waist with both arms at his sides. FIG. 9 illustrates an arm extension in which the individual raises both arms overhead with the palms facing downward. FIG. 10 illustrates arms overhead in which the individual raises both arms overhead with the palms facing forward. FIG. 11 illustrates the left trunk rotation in which the individual rotates at the hips with head turn movement. FIG. 12 illustrates a right trunk rotation in which the individual rotates to the right with a maximum range of motion at the hips and maximum range of head turn.

In a preferred embodiment of the invention in which there are eight second motion periods and eight second rest periods, the full pattern of electrodes 12 is sampled about fifteen (15) times per second so that there are at least four (4) groups of data for each eight second rest or activity period. These groups of measurements are stored in the computer memory processor 22. The sampling rates and groups of measurements are presented by way of example.

As stated above, patient disc 44 contains raw data and calculation results made generated by processor 22. These calculations made by processor 22 of include muscle activity ratios. That is, the data is stored in ratio format. The ratios are calculated as a percentage of muscle activity of the muscle activity for the most active muscle. These ratios are completed for each sample time. This ratio step is part of the data analysis step for this embodiment of the invention (step 140).

This ratio technique helps to eliminate many of the errors possible in taking surface electrical activity muscle measurements for muscle activity. For example, errors due to incorrect electrode placement, variations in skin resistances and other factors well known in the art which may affect an absolute measure of muscle activity will be partially filtered out by taking the ratio of different muscles throughout the back.

In accordance with an embodiment of the present invention, the next step is compiling the database of sets of measurements from a plurality of individuals for making diagnostic comparisons of data. This step of compiling a database includes the substep of repeating the step of collecting electrical muscle activity measurements for a number of individuals sufficient to develop a sample representative of a population. Preferably, a group of individuals is selected for collection of electrical muscle activity measurements. The individuals can be considered a normative set of individuals to which patients can be compared.

In another embodiment of this invention, a database of normal activity may be one of many databases for comparison purposes. That is, a normative database containing a population of individuals whose measurements are considered to be healthy and constitute a healthy population of individuals is not the only possible database available for comparison purposes. Additional databases having a sufficient number of individual's data who have been diagnosed as having muscle dysfunction may be established.

Figure 4:
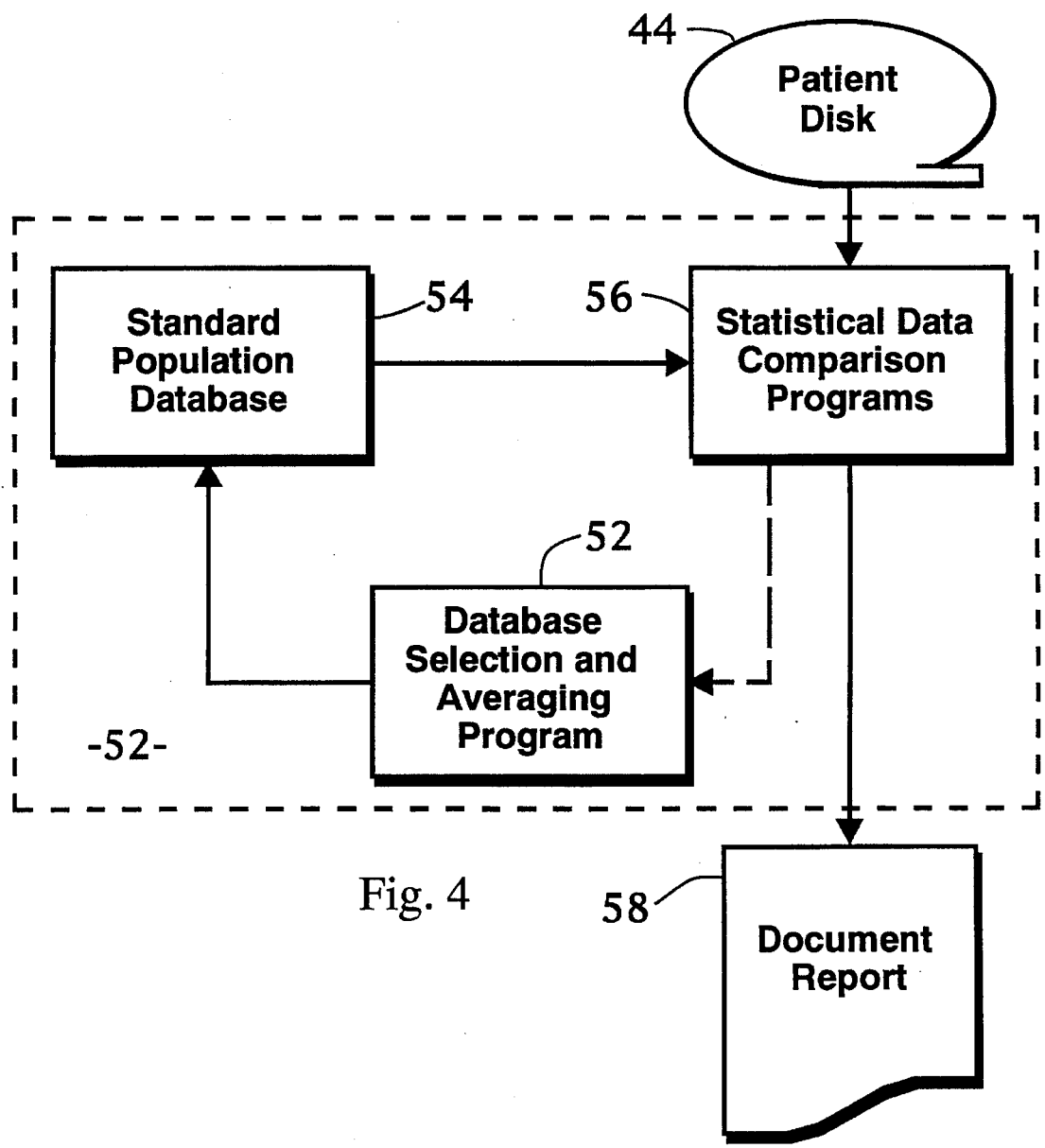
FIG. 4 is a block diagram illustrating additional components used in practice of the present preferred embodiment of the invention.

FIG. 4 shows a block diagram of a system used to compile database sets of measurements from individuals. Processor 50 may be used to practice this portion of this embodiment of the invention. Computer processor 50 can be a processor of known design such a personal computer or a mainframe system. Database selection and averaging program takes data from patient disc 44 and generates a standard population database 54.

A patient's disc 44 whose back muscle dysfunction is being determined is input into processor 50. The raw data and calculations of patient disc 44 are used by the statistical data comparison program in quantifying back muscle dysfunction for a patient in accordance with this invention. Accordingly, the electrical muscle activity measurements are collected for the patient whose discs 44 are being used to determine back muscle dysfunction, and electrical muscle activity measurement ratios taken from the patient's disc 44 are computed and then compared to the sample average ratios of the sample. Preferably, statistical data comparison program 56 makes the comparisons of the patient ratios to those of the sample determined by population data base 54.

Further, in quantifying back muscle dysfunction, the substep of determining a measure of back muscle dysfunction response to the comparison of the patient ratios is performed. Preferably, statistical data comparison program 56 returns a number of conclusions on which a diagnostic evaluation may be based.

The conclusions of statistical data comparison program 56 is based on the comparison of electrical activity measurements and can be based upon other factors. These other factors include relaxation time and change in relaxation time between activity and rest periods. Another indication of muscle health may be determined by the roughness of the measured signal. The adipose tissue correction factor is instrumental in making the comparison as discussed above.

The diagnostic conclusions generated by data comparison program 56 are output in a document report 58 (step 142). Document report 58 may report diagnostic conclusions and help determine a desirable therapeutic treatment.

In an alternative preferred embodiment, basically the same hardware components are utilized with minor exceptions. No calculations are performed by processor 22 and the raw data is sent to processor 50 where all data analysis takes place in the alternative preferred embodiment. The broad steps as illustrated in FIG. 13 are performed in the alternative preferred embodiment except that the data analysis for the alternative preferred embodiment is performed as described below and illustrated in FIGS. 14 and 15.

The data collected for patient analysis and compilation of the normative data base is collected during the time at which the subject pauses at the peak of the motion performed during a movement. After the data analysis begins (step 146) the data collected during each respective movement is averaged (step 148).

These data values are then adjusted for the adipose thickness underlying the corresponding electrode (step 152). The correction factor is computed by processor 50 by referring to a table which lists correction factors for given thicknesses of adipose tissue. The table is calculated from an empirically derived formula. This formula is a result of multivariant analysis conducted from the experimental results and stored in processor 50.

The identity and level of the dysfunctional muscles is determined by a procedure involving comparison of patient ratio data to sample ratio data stored in a sample data base, i.e. a normative data base (step 154). The determination of dysfunctional muscles procedure performs corresponding analysis for all muscles ($N_i$, i: i=1,N) and corresponding ratios ($R_h$, h: h=1,1-N) across all movements ($P_j$, j=1,P) (steps 158–162).

The logarithm of ratio $R_h$ is calculated for the adipose-corrected data value of the currently analyzed muscle $N_i$ with every other adipose-corrected data value of the other N-1 muscles for the current movement $P_j$ (step 164). Starting with a first ratio value $R_h$ (h=1), all the ratios ($R_h$: h=1,N-1) are compared to the sample values in the sample data base to determine if each ratio $R_h$ is abnormal (step 166). The comparison involves determining if the difference (z) between the patient's calculated ratio and the sample ratio is greater than two standard deviations (step 166).

If the ratio is abnormal then a kinesiological weighing factor $K_h$ is generated which is proportional to the kinesiological relationship between the corresponding muscles for ratio $R_h$ (step 168). Kinesiological weighing factor $K_h$ is an empirical value which represents a degree of structural relatedness or dependence for the corresponding muscles relative to the other muscles for corresponding movement $P_j$.

If the degree of abnormality is significant because the difference between the patient's logged ratio, log $R_h$, and the sample data base logged ratio is greater than three standard deviations (step 170), then kinesiological weighing factor $K_h$ is increased according to an expert system which adds a factor for muscles having a kinesiological significant relationship and select other muscle pairs as determined statistically (step 172). The statistical determination is significant when muscles which are not kinesiological related show some systematic correlation in data values.

A kinesiological relationship between muscles is the degree of structural "relatedness" that the two muscles share in terms of their role in supporting the back. A kinesiological matrix is established for the muscles in the back which defines the kinesiological weighing factor between muscles in the back for each movement $P_j$. This kinesiological matrix is developed based on structural and physiological principles.

Whether or not the difference (z) is significantly abnormal (step 170), kinesiological weighing factor $K_h$ developed thus far for abnormal ratio data $R_h$ is added to a total kinesiological weighing factor $K_i$ for corresponding muscle $N_i$ in current movement $P_j$ (step 174). The analysis of the ratio data for muscle $N_i$ in movement $P_j$ is repeated for N-1 ratios $R_h$ for all other muscles (h: 1, N-1)(steps 164, 166, 168, 170, 172, 174, 176,178).

After the all the ratios $R_h$ for muscle $N_i$ in the current movement $P_j$ are analyzed (step 178) and a total kinesiological weighing factor $K_i$ for muscle $N_i$ calculated, the evaluative significance for muscle $N_i$ in movement $P_j$ is determined (step 184). The total kinesiological weighing factor $K_i$ is limited by whether muscle $N_i$ contributes significantly in performing movement $P_j$, i.e. whether the behavior of muscle $N_i$ in this movement is relevant to its evaluation (step 182). A grade of severity is then assigned to the level of dysfunction of muscle $N_i$ in movement $P_j$ (step 184).

The process of ratio analysis and assignment of dysfunction level is repeated for movement $P_j$ for all muscles $N_i$ ($N_i$, i: i=1,N) (steps 164–188). After the data for all movements $P_j$ ($P_j$, j: j=1,P) is analyzed (steps 190, 192) then the degree of muscle dysfunction is determined based on the number of movements for which the muscle was dysfunctional and the severity of the dysfunction (step 194). In the preferred embodiment, the levels of dysfunction are classified as "serious", "significant", and "symptomatic". Serious dysfunction indicates a consistent high level of dysfunction and repetitive compensation patterns which are contributory to the patient's symptoms and require treatment. Significant dysfunction indicates a consistent level of abnormality which, while not as severe as serious dysfunction, is contributory to the patient's symptoms and requires treatment. Symptomatic dysfunction indicates symptoms of dysfunction which, if correlated to other clinical findings, may warrant treatment.

Figure 16:
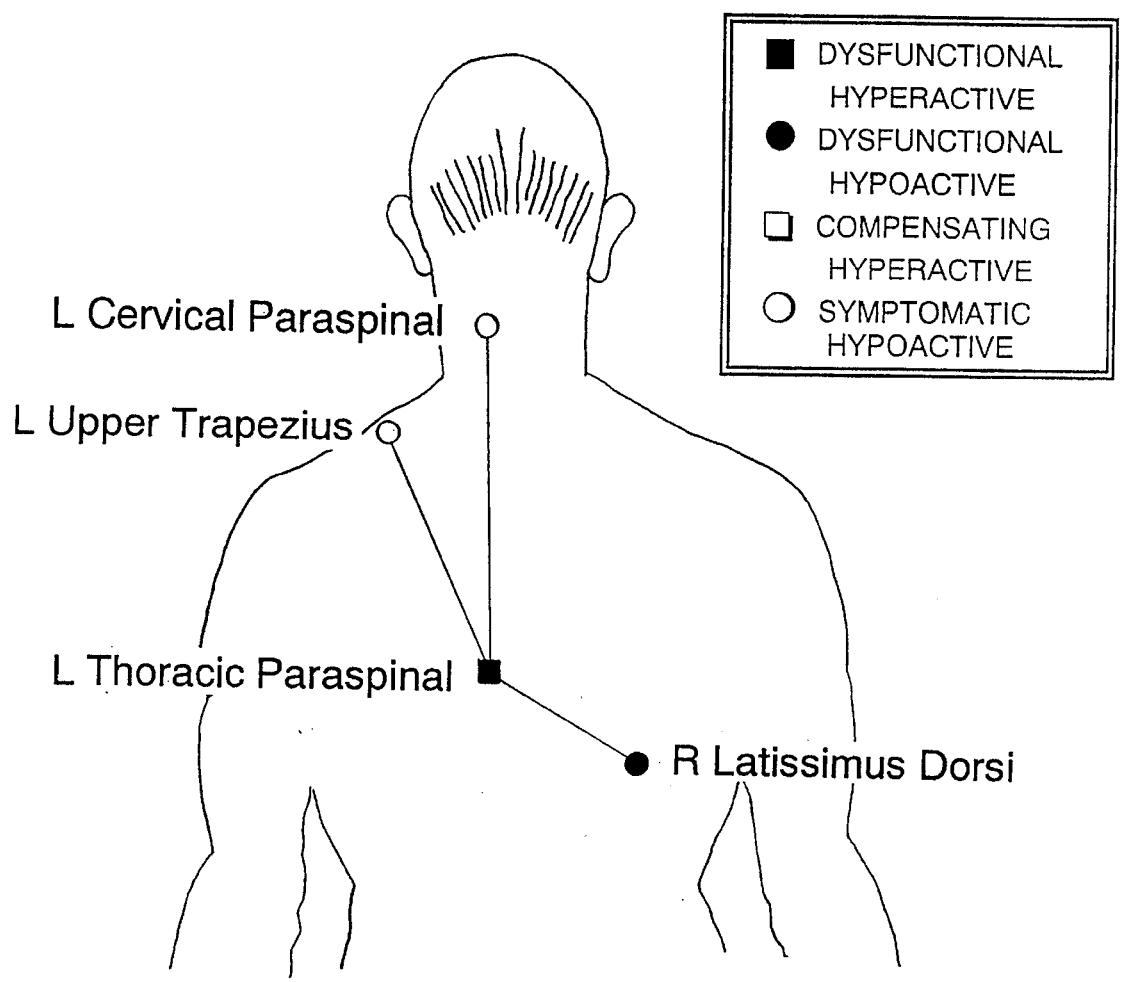
FIG. 16 is a diagram of an exemplary evaluation report for a patient experiencing back muscle dysfunction.

After the determination of the dysfunctional muscles, as illustrated in FIG. 15, the patterns of compensating relationships for dysfunctional muscles are mapped (step 198). These patterns are based on the muscle activity levels and the kinesiological relationships of the muscles. The mapped patterns graphically illustrate the muscle dysfunction and assist the physician in selecting an appropriate course of therapy. An illustrative example of a mapped pattern of dysfunction is shown in FIG. 16.

Processors 22, 50 disclosed above are understood to be known instrumentalities which include such conventional peripheral devices as electronic storage media such as a floppy disc drive. Likewise, disclosed hardware is controlled using conventional principles of electronic instrumentation control. Also, it should be noted that the determination of back muscle dysfunction in accordance with the present invention is applicable to other muscles, such as leg or abdominal muscles.

It should also be recognized that muscle activity can be equivalently measured by alternative techniques to the sEMG as the technology becomes feasible.

It will be apparent to those skilled in the art that various modifications, variations and additions can be made in the method for determining back muscle dysfunction of the present invention without departing from the scope or spirit of the invention. Thus, it is intended that the present invention cover the modifications, variations and additions provided that they come within the scope of the appended claims and their equivalents.

We claim:

1. A method for determining back muscle dysfunction of a patient, comprising the steps of:

(a) placing pairs of left and right electrodes in the areas adjacent pairs of upper, middle and lower back muscles, such as the cervical paraspinal muscles, the upper trapezius muscles, the middle trapezius muscles, the teres major muscles, the thoracic paraspinal muscles, the latissimus sorsi muscles, the obliquus externus muscles, and the lumbar paraspinal muscles, of the patient for measuring electrical muscle activities of the muscle areas thereof;

(b) choosing different patient positions that require different muscle activity that is normally bilaterally symmetric;

(c) choosing pairs of different patient positions that normally require different bilaterally reversed symmetric muscle activity;

(d) causing the patient to assume each of the patient positions for a fixed length of time;

(e) sampling the amplitudes of electrical activity of the patient multiple times with the electrodes during the time when the patient is in each of the plurality of patient positions, the electrical muscle activity simultaneously indicating the functionality and consequent compensating relationships of the muscles in the upper, middle and lower back of the patient;

(f) calculating ratio data by determining the logarithm ratio of selected and weighted measures of the electrical muscle activity to selected and weighted other measures of the electrical muscle activity for the patient;

(g) comparing the logarithmic ratios calculated for the patient to a database of average logarithmic ratios for a plurality of individuals having no symptomatic back dysfunction; and (h) determining from the magnitude of differences in the logarithmic ratio comparison whether back muscle dysfunction exists in the patient for each muscle area of the patient at which an electrode was placed.

2. The method for determining back muscle dysfunction of a patient according to claim 1, wherein step (h) includes:

detecting abnormal patient ratio data to determine if the absolute magnitude of the difference between abnormal patient ratio data and ratio data is greater than or equal to an empirically determined value.

3. The method for determining back muscle dysfunction of a patient according to claim 2, wherein step (e) includes:

(e1) sampling respective electrical muscle area activity for a plurality of corresponding muscles, and wherein step (f) includes:

(f1) calculating a plurality of ratios for a first muscle area, each of said ratios respectively including the ratio of a measure of electrical muscle activity of the first muscle area to a measure of electrical muscle activity of a selected one of the other muscle areas.

4. The method for determining back muscle dysfunction of a patient according to claim 3, wherein step (h) includes:

(h1) determining a measure of back muscle dysfunction derived from the kinesiological relationship between corresponding patient areas for abnormal ratio data.

5. The method for determining back muscle dysfunction of a patient according to claim 1 wherein step (h) includes:

(h1) determining a measure of back muscle dysfunction for each muscle area corresponding to abnormal ratio data within a movement.

6. The method for determining back muscle dysfunction of a patient according to claim 5, wherein step (h) includes:

(h2) determining the severity of dysfunction of a muscle area derived from the number of movements for which there is a measure of back muscle dysfunction for the muscle area and combined magnitude of corresponding measures of back muscle dysfunction for the muscle area.

7. The method defined in claim 1 wherein step (d) includes:

(d1) causing the patient to assume each of the fixed patient positions for a fixed length of time multiple times, and wherein step (e) includes:

(e1) sampling the amplitudes of electrical activity of the patient a plurality of times with the electrodes during the times when the patient is in each of the plurality of fixed positions.

8. The method defined in claim 1 including the additional step of:

(i) determining the impedance of the patient from the electrodes to the muscle areas, and wherein step (g) includes:

(g1) adjusting the measured amplitude of electrical activity in accordance with the determined impedance of the patient.

9. The method defined in claim 8 wherein the determination of step (i) includes:

(i1) measuring the thickness of the adipose layer of the patient to determine the impedance.

10. The method defined in claim 8 wherein the determination of step (i) includes:

(i1) measuring the thickness of the adipose layer of the patient to determine the impedance.

11. The method defined in claim 1 wherein step (h) includes:

(h1) determining from the magnitude of deviation in the logarithmic ratios, at least two levels of muscle dysfunction that indicate treatment is advisable and to what muscle areas.

12. The method defined in claim 11 wherein step (h) includes:

(h1) weighting the patient's logarithmic ratios for various muscle areas in accordance with the muscle areas kinesiological relationships so that the compensating relationships for the patient's dysfunctional muscles can be determined.

13. The method defined in claim 12 including the additional step of:

(i) mapping the severity of the patient's compensating relationships for each of the patient's positions to graphically illustrate the muscle dysfunction and assist in selection of an appropriate course of therapy.

14. The method defined in claim 12 wherein step (g) includes:

(g1) generating the database of average logarithmic ratios for a plurality of individuals having no symptomatic back dysfunction by for each of the plurality of individuals:

placing pairs of left and right electrodes thereon in the areas adjacent pairs of upper, middle and lower back muscles, that are to be used in patient testing;

causing the individual to assume each of the patient positions for the fixed length of time;

sampling the amplitudes of electrical activity of the individual multiple times with the electrodes during the time when the individual is in each of the plurality of patient positions;

calculating ratio data by determining the logarithm ratio of selected and weighted measures of the electrical muscle activity to selected and weighted other measures of the electrical muscle activity for the individual; and averaging the logarithmic ratios calculated for the individual into the database of average logarithmic ratios for a plurality of individuals having no symptomatic back dysfunction.

15. A method for determining back muscle dysfunction of a patient, comprising the steps of:

(a) placing pairs of left and right electrodes in the areas adjacent pairs of upper, middle and lower back muscles of the patient for measuring electrical muscle activities of the muscle areas thereof;

(b) choosing different patient positions that require different muscle activities that are normally bilaterally symmetric;

(c) choosing pairs of different patient positions that normally require different bilaterally reversed symmetric muscle activities;

(d) causing the patient to assume each of the patient positions for a fixed length of time;

(e) sampling the amplitudes of electrical activity of the patient multiple times with the electrodes during the time when the patient is in each of the plurality of patient positions, the electrical muscle activity simultaneously indicating the functionality and consequent compensating relationships of the muscles in the upper, middle and lower back of the patient;

(f) calculating ratio data by determining a function ratio of selected and weighted measures of the electrical muscle activity to selected and weighted other measures of the electrical muscle activity for the patient, the function emphasizing low electrical muscle activity with respect to high electrical muscle activity;

(g) comparing the function ratios calculated for the patient to a database of average function ratios for a plurality of individuals having no symptomatic back dysfunction; and (h) determining from the magnitude of differences in the function ratio comparison whether back muscle dysfunction exists in the patient for each muscle area of the patient at which an electrode was placed.

16. The method defined in claim 15 wherein step (d) includes:

(d1) causing the patient to assume each of the fixed patient positions for a fixed length of time multiple times, and wherein step (e) includes:

(e1) sampling the amplitudes of electrical activity of the patient a plurality of times with the electrodes during the times when the patient is in each of the plurality of fixed positions.

17. The method defined in claim 15 including the additional step of:

(i) determining the impedance of the patient from the electrodes to the muscle areas, and wherein step (g) includes:

(g1) adjusting the measured amplitude of electrical activity in accordance with the determined impedance of the patient.

18. The method defined in claim 15 wherein step (h) includes:

(h1) determining from the magnitude of deviation in the function ratios, at least two levels of muscle dysfunction that indicate treatment is advisable and to what muscle areas treatment should affect.

19. The method defined in claim 18 wherein step (h) includes:

(h1) weighting the patient's function ratios for various muscle areas in accordance with the muscle areas kinesiological relationships so that the compensating relationships for the patient's dysfunctional muscles can be determined.

20. The method defined in claim 19 including the additional step of:

(i) mapping the severity of the patient's compensating relationships for each of the patient's positions to graphically illustrate the muscle dysfunction and assist in selection of an appropriate course of therapy.

21. A method for determining back muscle dysfunction of a patient, comprising the steps of:

(a) placing pairs of left and right electrodes in the areas adjacent pairs of upper, middle and lower back muscles of the patient for measuring electrical muscle activities of the muscle areas thereof;

(b) choosing different patient positions that require different muscle activities to maintain such positions that are bilaterally symmetric in individuals without back muscle dysfunction;

(c) choosing pairs of different patient positions that require different bilaterally reversed symmetric muscle activities to maintain such positions in individuals without back muscle dysfunction;

(d) causing the patient to assume each of the patient positions for a fixed length of time;

(e) sampling and storing the amplitudes of electrical activity of the patient multiple times with the electrodes during the time when the patient is in each of the plurality of patient positions, the electrical muscle activity simultaneously indicating the functionality and consequent compensating relationships of the muscles in the upper, middle and lower back of the patient;

(f) calculating ratio data by determining a function ratio of selected and weighted measures of the electrical muscle activities to selected and weighted other measures of the electrical muscle activity for the patient, the function emphasizing low electrical muscle activity with respect to high electrical muscle activity;

(g) comparing the function ratios calculated for the patient to a database of average function ratios for a plurality of individuals having no symptomatic back dysfunction;

(h) determining from the magnitude of differences in the function ratio comparison whether abnormal back muscle activity exists in the patient for each muscle area of the patient at which an electrode was placed;

(i) if in step (h) abnormal back muscle activity is determined, then multiply the function ratio by a kinesiological weighting factor which corresponds to the kinesiological relationship between the muscle areas in the function ratio;

(j) determine if the determined abnormal back muscle activity is consistent with different patient positions; and (k) display consistently determined abnormal back muscle activity.

22. The method defined in claim 21 wherein step (e) includes:

(e1) determining the impedance of the patient from the electrodes to the muscle areas; and (e2) adjusting the stored amplitude of electrical activity in accordance with the determined impedance of the patient.

23. The method defined in claim 21 wherein step (k) includes:

(k1) displaying consistently determined hyperactive dysfunctional back muscle area activity;

(k2) displaying consistently determined hypoactive dysfunctional back muscle area activity;

(k3) displaying consistently determined compensating hyperactive back muscle area activity; and (k4) displaying consistently determined symptomatic hypoactive back muscle area activity.

\* \* \* \* \*